(12) United States Patent
Pilgeram et al.

(10) Patent No.: US 9,463,013 B2
(45) Date of Patent: Oct. 11, 2016

(54) ADJUSTABLE CONTINUOUS FILAMENT STRUCTURE AND METHOD OF MANUFACTURE AND USE

(71) Applicants: Stryker Corporation, Kalamazoo, MI (US); Cortland Cable Company, Inc., Cortland, NY (US)

(72) Inventors: Kyle Craig Pilgeram, San Jose, CA (US); Luis Padilla, Davidson, NC (US); Aaron Vodnick, East Greenwich, RI (US); Randy Longerich, Bellingham, WA (US)

(73) Assignees: Stryker Corporation, Kalamazoo, MI (US); Cortland Cable Company, Inc., Cortland, NY (US)

( * ) Notice: Subject to any disclaimer, the term of this patent is extended or adjusted under 35 U.S.C. 154(b) by 488 days.

(21) Appl. No.: 13/799,773

(22) Filed: Mar. 13, 2013

(65) Prior Publication Data
US 2014/0277121 A1    Sep. 18, 2014

(51) Int. Cl.
| | |
|---|---|
| A61B 17/06 | (2006.01) |
| A61B 17/04 | (2006.01) |
| B65H 69/06 | (2006.01) |
| D02G 3/44 | (2006.01) |

(52) U.S. Cl.
CPC ..... *A61B 17/06166* (2013.01); *A61B 17/0401* (2013.01); *A61B 17/0469* (2013.01); *A61B 17/0485* (2013.01); *B65H 69/06* (2013.01); *D02G 3/448* (2013.01); *A61B 2017/0404* (2013.01); *A61B 2017/0462* (2013.01); *A61B 2017/0496* (2013.01)

(58) Field of Classification Search
CPC   A61B 17/04; A61B 17/06; A61B 17/06166; A61B 17/0483; A61B 17/0469
USPC ......................... 606/228, 213, 139
See application file for complete search history.

(56) References Cited

U.S. PATENT DOCUMENTS

| | | |
|---|---|---|
| 749,624 A | 1/1904 | McCullough |
| 1,308,798 A | 7/1919 | Masland |
| 1,624,530 A | 4/1927 | Caruso |

(Continued)

FOREIGN PATENT DOCUMENTS

| | | |
|---|---|---|
| DE | 3131496 A1 | 2/1983 |
| DE | 4231101 A1 | 3/1994 |

(Continued)

OTHER PUBLICATIONS

BIOMET Sports Medicine: Micromax Flex Suture Anchor, (2008).

(Continued)

*Primary Examiner* — Victor Nguyen
(74) *Attorney, Agent, or Firm* — Lerner, David, Littenberg, Krumholz & Mentlik, LLP

(57) ABSTRACT

A method of assembling an adjustable continuous filament assembly whereby a single length of filament is spliced to form a nonadjustable portion and a single free segment. The single free segment is introduced into the inner core of the nonadjustable portion at a first position. The single free segment is passed through at least a portion of the inner core of the nonadjustable portion. The single free segment is withdrawn from the nonadjustable portion at a second position, thereby forming an adjustable portion secured to the nonadjustable portion and adjustable by the single free segment.

20 Claims, 7 Drawing Sheets

(56) References Cited

U.S. PATENT DOCUMENTS

| | | |
|---|---|---|
| 2,073,903 A | 3/1937 | O'Neil |
| 2,267,925 A | 12/1941 | Johnston |
| 2,382,019 A | 8/1945 | Miller |
| 2,494,229 A | 1/1950 | Collison |
| 2,515,365 A | 7/1950 | Zublin |
| 2,547,571 A | 4/1951 | Ettinger |
| 2,808,632 A | 10/1957 | Cline |
| 2,833,284 A | 5/1958 | Springer |
| 3,384,085 A | 5/1968 | Hall |
| 3,461,875 A | 8/1969 | Hall |
| 3,554,192 A | 1/1971 | Isberner |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,608,972 A | 9/1986 | Small |
| 4,611,515 A | 9/1986 | Marbourg, Jr. |
| 4,646,738 A | 3/1987 | Trott |
| 4,706,659 A | 11/1987 | Matthews et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,860 A | 6/1995 | Lizardi et al. |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A * | 8/1996 | Kensey et al. ................ 606/213 |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,695 A | 12/1996 | Lal Sachdeva et al. |
| 5,584,835 A | 12/1996 | Greenfield |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,674,279 A | 10/1997 | Wright et al. |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,702,397 A | 12/1997 | Goble et al. |
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,541 A | 3/1998 | Anspach, III et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,797,918 A | 8/1998 | McGuire et al. |
| 5,810,825 A | 9/1998 | Huebner |
| 5,814,056 A | 9/1998 | Prosst et al. |
| 5,836,953 A | 11/1998 | Yoon |

(56) References Cited

U.S. PATENT DOCUMENTS

| | | |
|---|---|---|
| 5,846,254 A * | 12/1998 | Schulze et al. ............ 606/148 |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,897,574 A | 4/1999 | Bonutti |
| 5,906,626 A | 5/1999 | Carrillo |
| 5,921,986 A | 7/1999 | Bonutti |
| 5,928,244 A | 7/1999 | Tovey et al. |
| 5,941,139 A | 8/1999 | Vodehnal |
| 5,948,002 A | 9/1999 | Bonutti |
| 5,951,559 A | 9/1999 | Burkhart |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,296,659 B1 | 10/2001 | Foerster |
| 6,306,138 B1 | 10/2001 | Clark et al. |
| 6,306,159 B1 | 10/2001 | Schwartz et al. |
| 6,343,482 B1 | 2/2002 | Endo et al. |
| 6,352,538 B2 | 3/2002 | McGuire et al. |
| 6,358,253 B1 | 3/2002 | Torrie et al. |
| 6,419,678 B1 | 7/2002 | Asfora |
| 6,419,684 B1 | 7/2002 | Heisler et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,740,090 B1 | 5/2004 | Cragg et al. |
| 6,780,188 B2 | 8/2004 | Clark et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,863,672 B2 | 3/2005 | Reiley et al. |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,025,770 B2 | 4/2006 | McGuire et al. |
| 7,029,490 B2 | 4/2006 | Grafton et al. |
| 7,048,754 B2 | 5/2006 | Martin et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,285,124 B2 | 10/2007 | Foerster |
| 7,309,338 B2 | 12/2007 | Cragg |
| 7,326,215 B2 | 2/2008 | Myers et al. |
| 7,331,263 B2 | 2/2008 | Erickson et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,803,173 B2 | 9/2010 | Burkhart et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,256 B2 | 2/2011 | Grafton et al. |
| 7,901,431 B2 | 3/2011 | Shurnas |
| 7,905,903 B2 | 3/2011 | Stone et al. |
| 7,905,904 B2 | 3/2011 | Stone et al. |
| 7,909,851 B2 | 3/2011 | Stone et al. |

(56) References Cited

U.S. PATENT DOCUMENTS

| | | |
|---|---|---|
| 7,914,539 B2 | 3/2011 | Stone et al. |
| 7,918,874 B2 | 4/2011 | Siegal |
| 7,959,650 B2 * | 6/2011 | Kaiser et al. ............... 606/232 |
| 7,981,117 B2 | 7/2011 | Newton et al. |
| 7,981,140 B2 | 7/2011 | Burkhart |
| 7,993,369 B2 | 8/2011 | Dreyfuss |
| 8,002,733 B2 | 8/2011 | Kraft et al. |
| 8,043,253 B2 | 10/2011 | Kraft et al. |
| 8,057,500 B2 | 11/2011 | Mitusina |
| 8,088,130 B2 | 1/2012 | Kaiser et al. |
| 8,114,088 B2 | 2/2012 | Miller |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,398,678 B2 | 3/2013 | Baker et al. |
| 8,439,976 B2 | 5/2013 | Albertorio et al. |
| 8,460,379 B2 | 6/2013 | Albertorio et al. |
| 8,562,645 B2 | 10/2013 | Stone et al. |
| 8,591,578 B2 | 11/2013 | Albertorio et al. |
| 8,623,051 B2 | 1/2014 | Bojarski et al. |
| 8,663,324 B2 | 3/2014 | Schmieding et al. |
| 2002/0019635 A1 | 2/2002 | Wenstrom et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0193217 A1 | 9/2004 | Lubbers et al. |
| 2004/0260300 A1 | 12/2004 | Gorensek et al. |
| 2004/0267277 A1 | 12/2004 | Zannis et al. |
| 2005/0015153 A1 | 1/2005 | Goble et al. |
| 2005/0033362 A1 | 2/2005 | Grafton |
| 2005/0070906 A1 | 3/2005 | Clark et al. |
| 2005/0080400 A1 | 4/2005 | Corcoran et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0074434 A1 | 4/2006 | Wenstrom et al. |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0260259 A1 | 11/2007 | Fanton et al. |
| 2007/0288031 A1 | 12/2007 | Dreyfuss et al. |
| 2008/0004659 A1 | 1/2008 | Burkhart et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0071282 A1 | 3/2008 | Assell et al. |
| 2008/0109037 A1 | 5/2008 | Steiner et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140116 A1 | 6/2008 | Bonutti |
| 2008/0147063 A1 | 6/2008 | Cauldwell et al. |
| 2008/0147064 A1 | 6/2008 | Cauldwell et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0249481 A1 | 10/2008 | Crainich et al. |
| 2008/0255613 A1 | 10/2008 | Kaiser et al. |
| 2008/0275431 A1 | 11/2008 | Stone et al. |
| 2008/0306483 A1 | 12/2008 | Iannarone |
| 2008/0312689 A1 | 12/2008 | Denham et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli et al. |
| 2009/0157081 A1 | 6/2009 | Homan et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0248029 A1 | 10/2009 | Paulos |
| 2009/0306671 A1 | 12/2009 | McCormack et al. |
| 2009/0306711 A1 | 12/2009 | Stone et al. |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0318961 A1 | 12/2009 | Stone et al. |
| 2009/0326538 A1 | 12/2009 | Sennett et al. |
| 2010/0049196 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0121332 A1 | 5/2010 | Crainich et al. |

(56) References Cited

U.S. PATENT DOCUMENTS

| | | |
|---|---|---|
| 2010/0121333 A1 | 5/2010 | Crainich et al. |
| 2010/0145384 A1 | 6/2010 | Stone et al. |
| 2010/0152739 A1 | 6/2010 | Sidebotham et al. |
| 2010/0160962 A1 | 6/2010 | Dreyfuss et al. |
| 2010/0185238 A1 | 7/2010 | Cauldwell et al. |
| 2010/0185283 A1 | 7/2010 | Baird et al. |
| 2010/0191241 A1 | 7/2010 | McCormack et al. |
| 2010/0211075 A1 | 8/2010 | Stone |
| 2010/0241121 A1 | 9/2010 | Logan et al. |
| 2010/0249786 A1 | 9/2010 | Schmieding et al. |
| 2010/0268275 A1 | 10/2010 | Stone et al. |
| 2010/0292732 A1 | 11/2010 | Hirotsuka et al. |
| 2010/0292792 A1 | 11/2010 | Stone et al. |
| 2010/0305709 A1 | 12/2010 | Metzger et al. |
| 2011/0015674 A1 | 1/2011 | Howard et al. |
| 2011/0015675 A1 | 1/2011 | Howard et al. |
| 2011/0022083 A1 | 1/2011 | Dimatteo et al. |
| 2011/0022084 A1 | 1/2011 | Sengun et al. |
| 2011/0054526 A1 | 3/2011 | Stone et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264138 A1 | 10/2011 | Avelar et al. |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0150203 A1 | 6/2012 | Brady et al. |
| 2012/0150297 A1 | 6/2012 | Denham et al. |
| 2012/0150301 A1 | 6/2012 | Gamache et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0180291 A1 | 7/2012 | Oren et al. |
| 2012/0197271 A1 | 8/2012 | Astorino et al. |
| 2012/0203288 A1 | 8/2012 | Lange et al. |
| 2012/0209325 A1 | 8/2012 | Gagliano et al. |
| 2012/0245585 A1 | 9/2012 | Kaiser et al. |
| 2012/0253355 A1 | 10/2012 | Murray et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0165972 A1 | 6/2013 | Sullivan |
| 2013/0190818 A1 | 7/2013 | Norton |
| 2013/0190819 A1 | 7/2013 | Norton |
| 2013/0237997 A1 | 9/2013 | Arai et al. |
| 2013/0245700 A1 | 9/2013 | Choinski |
| 2013/0268000 A1 | 10/2013 | Harner et al. |
| 2013/0296931 A1 | 11/2013 | Sengun |
| 2013/0317544 A1 | 11/2013 | Ferguson et al. |
| 2013/0345749 A1 | 12/2013 | Sullivan et al. |

FOREIGN PATENT DOCUMENTS

| | | |
|---|---|---|
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 0611551 A1 | 8/1994 |
| EP | 1155776 A2 | 11/2001 |
| EP | 1369089 A2 | 12/2003 |
| EP | 2544607 A1 | 1/2013 |
| EP | 2548519 A2 | 1/2013 |
| FR | 1166884 A | 11/1958 |
| FR | 2606996 A1 | 5/1988 |
| FR | 2676638 A1 | 11/1992 |
| GB | 2093353 A | 9/1982 |
| WO | 9511631 A1 | 5/1995 |
| WO | 00/44291 A1 | 8/2000 |
| WO | 0128457 A1 | 4/2001 |
| WO | 03007861 A1 | 1/2003 |
| WO | 2007/010389 A1 | 1/2007 |
| WO | 2008128075 A1 | 10/2008 |
| WO | 2009105880 A1 | 9/2009 |
| WO | 2011112371 A1 | 9/2011 |
| WO | 2012134999 A1 | 10/2012 |
| WO | 2012158583 A1 | 11/2012 |

OTHER PUBLICATIONS

Burkinshaw, U.S. Appl. No. 60/418,545, filed Oct. 15, 2002.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
Cole et al., American Journal of Sports Medicine, vol. XX, No. X, 2011.
CONME: LINVATEC: Shoulder Restoration System Y-Knot 1.3mm All Suture Anchor, © 2011 Linvatec Corporation, a subsidiary of ConMed Corporation—CBR 3057 (4 pages).
European Search Report, EP 10173568, dated Nov. 30, 2010.
HHS Tube, Fort Wayne Metals Research Products Corp., 2009.
International Search Report PCT/US2010/042264, dated Sep. 30, 2010.
Medtronic, The VISAO High-Speed Otologic Drill Catalog, 2007.
Perthes, German Surgery Periodical, vol. 85, Commemmorative Publication, pp. 2-18, 1906.
Perthes, Ober Operationen bel habitueller Schulterluxaton, X, pp. 199-227, 85.

(56) References Cited

OTHER PUBLICATIONS

Sugaya et al., Journal of Bone and Joint Surgery, vol. 85-A, No. 5, pp. 878-884, May 2003.
U.S. Appl. No. 13/368,730, filed Feb. 8, 2012.
U.S. Appl. No. 13/588,592, filed Aug. 17, 2012.
U.S. Appl. No. 13/783,804, filed Mar. 4, 2013.
U.S. Appl. No. 61/679,336, filed Aug. 3, 2012.
U.S. Appl. No. 13/085,882, filed Apr. 13, 2011.
U.S. Appl. No. 13/588,586, filed Aug. 17, 2012.
U.S. Appl. No. 13/303,849, filed Nov. 23, 2011.
Canadian Office Action for Application No. 2768020 dated Jan. 21, 2014.
Australian Examination Report for Application No. 2013202699 dated Feb. 21, 2014.
Extended European Search Report for Application No. EP 12164104 dated Jul. 11, 2012.
Extended European Search Report for Application No. EP14159656 dated Jun. 6, 2014.

\* cited by examiner

ADJUSTABLE CONTINUOUS FILAMENT STRUCTURE AND METHOD OF MANUFACTURE AND USE

BACKGROUND OF THE INVENTION

The use of continuous, closed suture loops has been incorporated in soft tissue surgeries in recent years, particularly since the proliferation of the use of knotless anchors. The decrease in the number of knots needed in a surgery is important as there is always a chance a knot may loosen or come undone, thereby compromising the repair. Additionally, the knot itself can create a weakened area which may result in a higher incidence of suture breakage.

Currently, a challenge in the suture art is developing a continuous suture loop that can be affixed to a suture anchor, tissue, or the like in an efficient manner. For example, issues tend to arise when using continuous suture loops when an operator (e.g., a surgeon or the like) attempts to obtain a desired tension on the soft tissue. This is particularly difficult in a repair of a torn anterior cruciate ligament (ACL) in a knee of a patient. In such a repair, the operator must properly tension the replacement ACL graft to ensure a successful result. When a standard continuous suture loop is used to fix the graft in a bone tunnel in the femur (via a suture button, as is known in the art), the operator can only control the tension by tensioning the graft, and affixing the graft at the desired tension, in a bone tunnel in the tibia. This is often times difficult to achieve and thus, has a tendency to reduce the effectiveness of such repairs. Additionally, when a standard continuous suture loop is utilized, the operator must carefully select the appropriate loop length and tunnel depth based on the size of the graft and the patient's anatomy, which may increase the risk of error or increase procedure length. Furthermore, current continuous suture loops can be difficult to secure to a suture anchor, suture button, or the like.

Presently, certain adjustable suture loops may be formed from multiple strands of suture and utilize a variety of external structures, such as sleeves, to form the adjustable portion structure. Other adjustable portion devices may be formed from a single strand of suture, which is typically folded along its length, sometimes multiple times, resulting in multiple free strands and a maze of filament running in multiple directions. Further, these adjustable portions may also utilize external structures to hold its configuration in place. The cacophony of filament produced by these devices in conjunction with external structures may increase the likelihood of snagging and increase the number of components, thereby increasing the probability of failure of one of these components. Further, the surgeon must divert his or her focus in order to ensure the adjustable suture loop does not become entangled with itself or other structures, oftentimes with limited success.

Thus, there is a need for a knotless, continuous, adjustable, closed suture structure, such as a loop, that is reliable and easy to use.

BRIEF SUMMARY OF THE INVENTION

Generally, the present invention includes devices, assemblies, systems, kits and methods of manufacture, assembly and use for the repair of soft tissue. Specifically, in one embodiment, the present invention includes a suture device constructed of a continuous filament having a continuous, adjustable loop configuration. Further, the adjustable loop configuration can be adjusted using a single free strand which may provide for simplified, reliable use in the repair of soft tissue, such as, in one embodiment, securing an ACL graft within a bone tunnel.

Furthermore, in other embodiments, the suture device may be combined with a suture anchor, such as a button anchor or the like, to form a system or kit for the repair of soft tissue. Such a kit may further include a plurality of suture devices and/or a plurality of suture anchors. Each suture anchor may be packaged, and arrive to the operator, fixedly secured to at least one suture device, though the suture anchor and suture device may also be packaged separately for assembly by the operator.

According to a first embodiment of the present invention, a method of assembling an adjustable continuous filament assembly, including splicing a single length of filament, thereby forming a nonadjustable portion and a single free segment. Further included in the method is introducing the single free segment into an inner core of the nonadjustable portion at a first position. Additionally, the method includes passing the single free segment through at least a portion of the inner core of the nonadjustable portion. The method also includes withdrawing the single free segment from the nonadjustable portion at a second position, thereby forming an adjustable portion secured to the nonadjustable portion and adjustable by the single free segment.

Further, the splicing step is performed by using a locking Brummel splice, stitched buried splice, a lock stitch tuck splice or the like. Additionally, the steps of introducing and passing of the single free segment through at least a portion of the inner core of the nonadjustable portion can form a one-way feature such that the free segment can be tensioned to shrink the adjustable portion, but may prevent the adjustable portion from expanding due to tension applied to the adjustable portion. Further, the first position and second position may be spaced from one another along the nonadjustable portion.

Continuing with this embodiment, the method may include the additional step of positioning the nonadjustable portion within a throughbore of a suture anchor. The method may also include the step of positioning an insert within the nonadjustable portion. Further, the method may include the step of engaging the suture anchor with the insert to secure the nonadjustable portion to the suture anchor.

According to another embodiment of the present invention, a continuous filament assembly including a single line of filament. The single line of filament includes a nonadjustable portion, an adjustable portion, and a single free segment. The adjustable portion includes a first portion and a second portion. The first portion extends from the nonadjustable portion to a first position along an outer wall of the nonadjustable portion, and the second portion enters into the outer wall of the nonadjustable portion and extends through at least a portion of an inner core of the nonadjustable portion to a second position along the outer wall of the nonadjustable portion. The single free segment extends from the outer wall of the nonadjustable portion at the second position such that the free segment is continuous with the second portion of the adjustable portion. Pulling the free segment shrinks the first portion of the adjustable portion.

Further, the nonadjustable portion may be formed by a locking splice. More specifically, the nonadjustable portion may be formed by a locking Brummel splice, stitched buried splice, a lock stitch tuck splice, or the like. Additionally, the positioning of the second portion of the adjustable portion through the inner core of the nonadjustable portion may form a one-way feature such that the free segment is tensionable to shrink the adjustable portion, but the one-way feature may prevent the adjustable portion from expanding due to tension applied to the adjustable portion. Further, the first position and second position may be spaced from one another along the nonadjustable portion.

Continuing with this embodiment, the assembly may additionally include a suture anchor disposed along a portion of the outer wall of the nonadjustable portion. Further, this anchor may be a button anchor. However, the anchor may also be a filamentary sleeve.

In a further embodiment of the present invention, a method of positioning, securing and tensioning a replacement ACL graft within a tunnel extending through a femur using a continuous adjustable filament device. The method includes introducing to the tunnel a single line of filament. The single line of filament includes a nonadjustable portion, an adjustable portion, a single free segment, and a button anchor. The button anchor is secured to the nonadjustable portion, and the graft is positioned through the adjustable portion. Additionally, the method includes passing the filament, anchor and graft into a femoral tunnel such that the anchor engages a lateral cortex of the femur. Also included in the method is securing the graft within a tibial tunnel. Further included in the method is tensioning the single free segment to shrink the adjustable portion and tension the graft between the tibial tunnel and the anchor.

Further, the single free segment may extend through the femoral tunnel adjacent the graft. Additionally, the step of securing the graft within the tibial tunnel may include securing the graft by a second single line of filament. The single line of filament may include a nonadjustable portion, an adjustable portion, and a single free segment. A second button anchor and the nonadjustable portion may be secured to the button anchor such that the graft is positioned through the adjustable portion of the second filament.

Additionally, the method may include the step of passing the second filament, second anchor and graft into tibial tunnel such that the second anchor engages a lateral cortex of the tibia. Also, the method may include the step of tensioning the single free segment of the second filament to shrink the adjustable portion of the second filament and further tension the graft between the anchor and second anchor.

Continuing with this embodiment, the single line of filament may include a one-way feature such that the single free segment can be tensioned to shrink the adjustable portion, but the one-way feature may prevent the adjustable portion from expanding due to tension applied to the adjustable portion.

In another embodiment of the present invention, a method of positioning tissue against bone using a continuous adjustable filament device. The method includes obtaining a single line of filament, which includes a nonadjustable portion, an adjustable portion, single free segment, and a suture anchor. The suture anchor may be secured to the single line of filament. Additionally, the method includes passing at least a portion of the adjustable portion through the tissue. Further included in the method is passing the nonadjustable portion and suture anchor through the adjustable portion passed through the tissue. Also included is inserting the suture anchor into the bone. The method also includes tensioning the single free segment to shrink the adjustable portion, thereby positioning the tissue against the bone.

Further, the single line of filament may include a one-way feature such that the single free segment can be tensioned to shrink the adjustable portion, but the one-way feature may prevent the adjustable portion from expanding due to tension applied to the adjustable portion.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
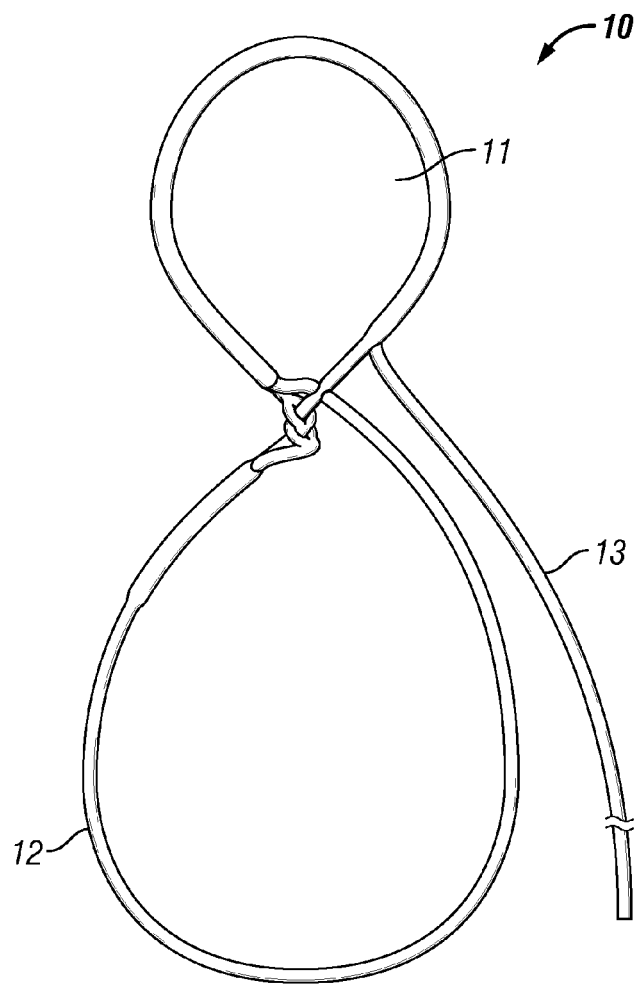
FIG. 1 shows one embodiment of a continuous, adjustable suture device having a nonadjustable portion, adjustable portion, and single free strand.

FIG. 1 depicts one embodiment of a suture device or assembly 10. As shown, suture device 10 includes a nonadjustable portion 11, an adjustable portion 12, and a single free strand 13. The suture device 10 may be constructed from a single, continuous, line of filament, preferably with a hollow core along at least a portion of its length. As used herein, "filament" or "filamentary" is defined as a suture or other thread-like material having a hollow core along at least a portion of its length. Preferably, the "filament" is a braided suture having a hollow core along its length. As used herein, "continuous" is defined as a single length of material, or preferably, s single length of braided, hollow suture. The single line of filament may be constructed from homogenous or heterogeneous materials such as, but not limited to, polyester, polyethylene (including ultra-high molecular weight polyethylene (UHMWPE)), polytetrafluorethylene (including expanded polytetrafluorethylene), nylon, polypropylene, aramids (such as Kevlar-based materials), polydioxanone, polygycolic acid, liquid crystal polymer (LCP), organic material (silk, animal tendon, or the like), metallic wire, or any combination of these materials. Preferably, suture device 10 is composed of suture, and specifically a blend of UHMWPE and polyester.

The free strand 13 may be tensioned by the operator to adjust the length of the adjustable portion 12. In the illustrated embodiment, where the adjustable portion 12 is in the configuration of an adjustable loop 12, tensioning of free strand 13 would adjust the diameter of the adjustable loop 12. The configuration of device 10 allows for one-way locking of the adjustable portion 12 such that the free strand 13 may be tensioned as desired by the operator to freely reduce the diameter of the adjustable portion (i.e., adjustable loop) 12. However, if tension is applied to the adjustable portion 12, the adjustable portion will not freely expand in length or diameter. This is important as the soft tissue is typically secured via the adjustable portion 12, as will be discussed further below. While the preferred embodiment of adjustable portion 12 and nonadjustable portion 11 are in the form of adjustable loop 12 and nonadjustable loop 11, respectively (as illustrated throughout FIGS. 1-12, generally), it is envisioned that these portions 11, 12 may be assembled in different shapes, configurations, etc.

Figure 2:
FIG. 2 shows a diagrammatic view of a single length of filament with reference points A, B, C, and D.

FIGS. 2-10 illustrate one method of assembly of suture device 10 from a single line of filament. FIG. 2 illustrates the single line of filament with reference points A, B, C, and D that form three line segments of which include short segment 14 and a long segment 13'.

Figure 4:
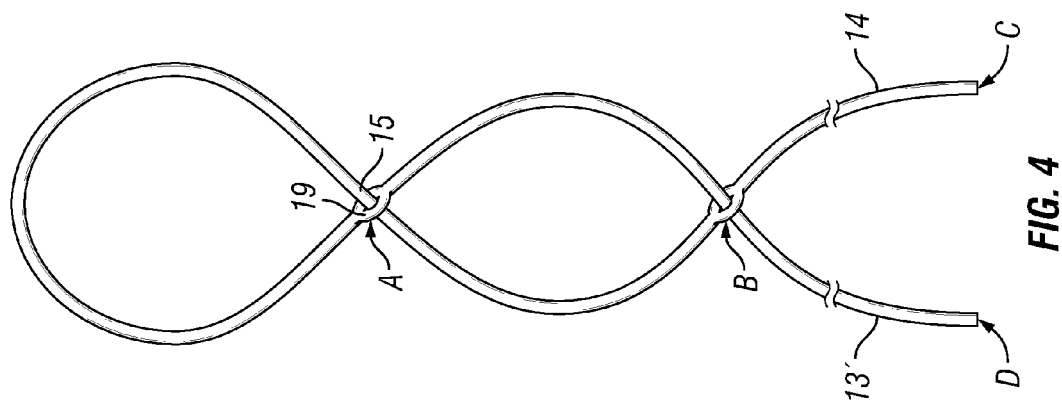
FIGS. 3-7 show subsequent steps of an exemplary method for forming the nonadjustable portion and single free strand of FIG. 1.
Figure 3:
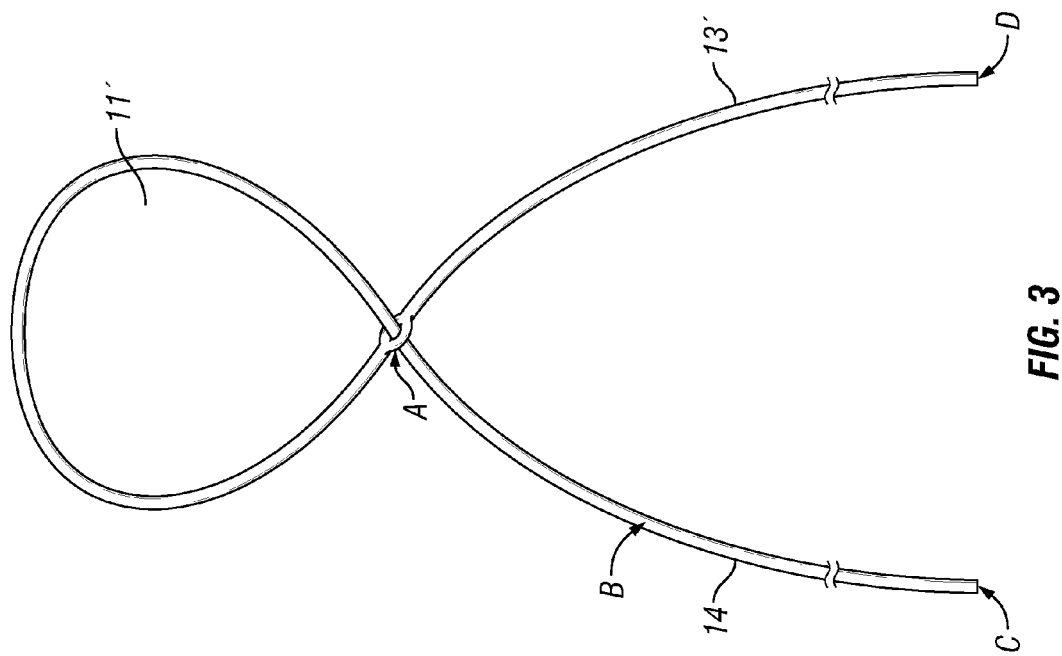
Figure 5:
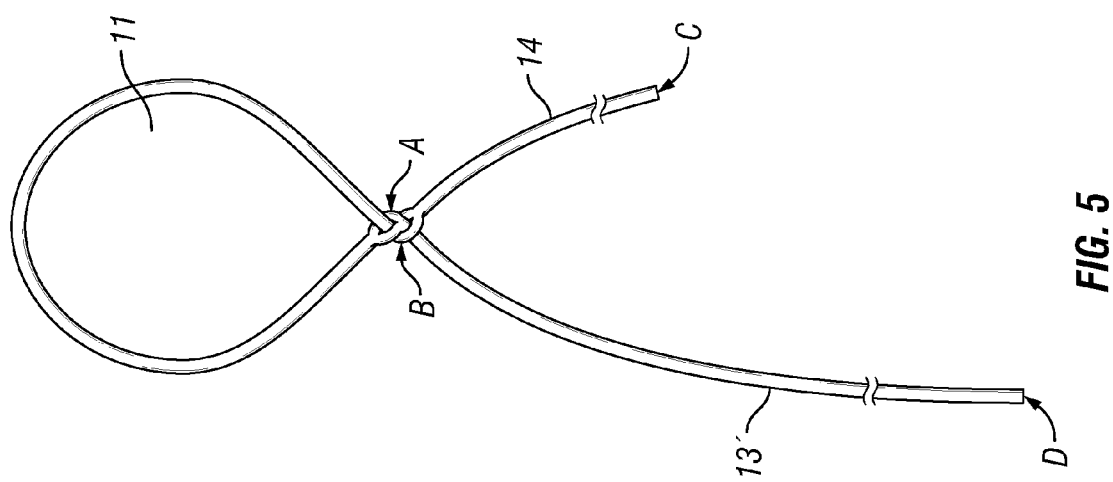

FIGS. 3-7 illustrate an exemplary method for forming the nonadjustable portion 11 utilizing a locking Brummel splice, as known in the art. While a locking Brummel splice is depicted, it is merely an example. Any locking or otherwise nonadjustable splice may be used besides a Brummel splice, such as a stitched buried splice, a lock stitch tuck splice, or the like. Referring to FIGS. 2 and 3, short segment 14 is passed through the braiding (i.e., the braiding of the braided hollow suture) at point A such that reference points B and C are passed through point A, which creates transient portion 11', illustrated as transient loop 11'. The long segment 13' is then passed through the braiding of the single line of filament at point B, as seen in FIG. 4. Points A and B are then cinched together forming the nonadjustable portion 11, as shown in FIG. 5.

Cinching of points A and B can be achieved by expanding transient portion 11' and pulling points C and D further apart. While this is occurring, reference points A and B can slide along the respective filaments passing through them. The direction of travel of A and B oppose each other resulting in A and B coming together to interfere with further travel. Once A and B interfere, the long segment 13' and short segment 14 are tensioned, which results in the constricting of the braiding at points A and B around the portion of respective filaments passing through them. This interference and tensioning can form a firm lock effectively prohibiting the expansion and contraction of the transient portion 11', thus forming nonadjustable portion 11, again, illustrated as nonadjustable loop 11.

Figure 6:
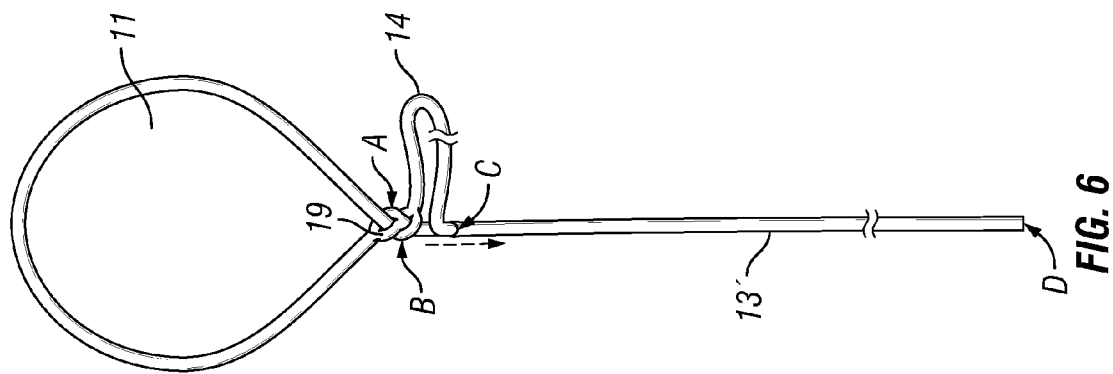
Figure 7:
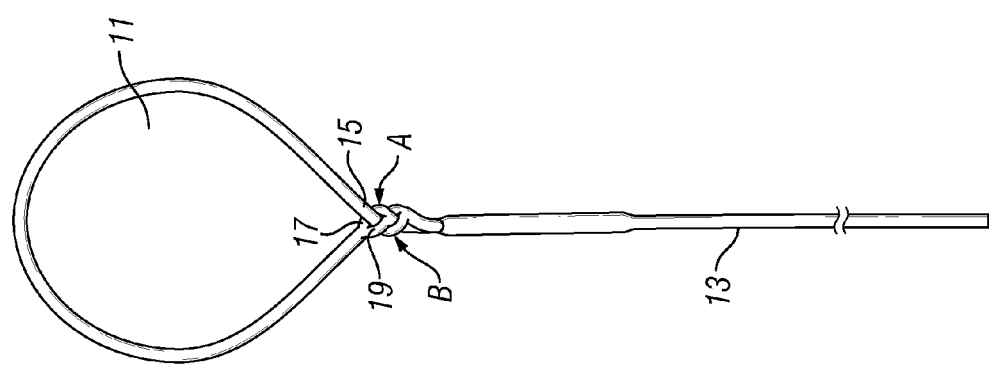

Once the nonadjustable portion 11 is formed, the short segment 14 is buried within the long segment 13', specifically within a hollow core of segment 13', as shown in FIG. 6. While it is preferred, as illustrated, that segment 14 be completely buried within segment 13' (and indeed, since segment 14 is shorter, this should be the case), segment 14 could alternatively extend out of segment 13'. The result of this step is a locking Brummel splice that converts the long segment 13' into the single free strand 13 and forms the nonadjustable portion 11 as shown in FIG. 7. It should be noted that the free strand 13 now has a "double thickness" including segment 14 within the core of long segment 13'. Such double thickness can provide additional strength to the adjustable portion 12 (the assembly of which is discussed below) which can be important once tension is applied thereto by a graft or other structure.

Figure 8:
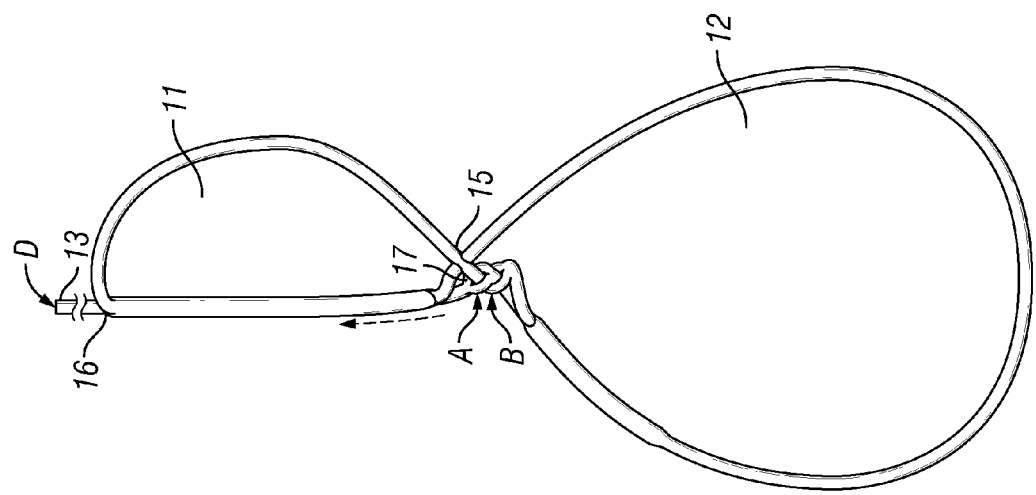
FIGS. 8-10 show subsequent steps of an exemplary method for forming the adjustable portion and single free strand of FIG. 1.
Figure 9:
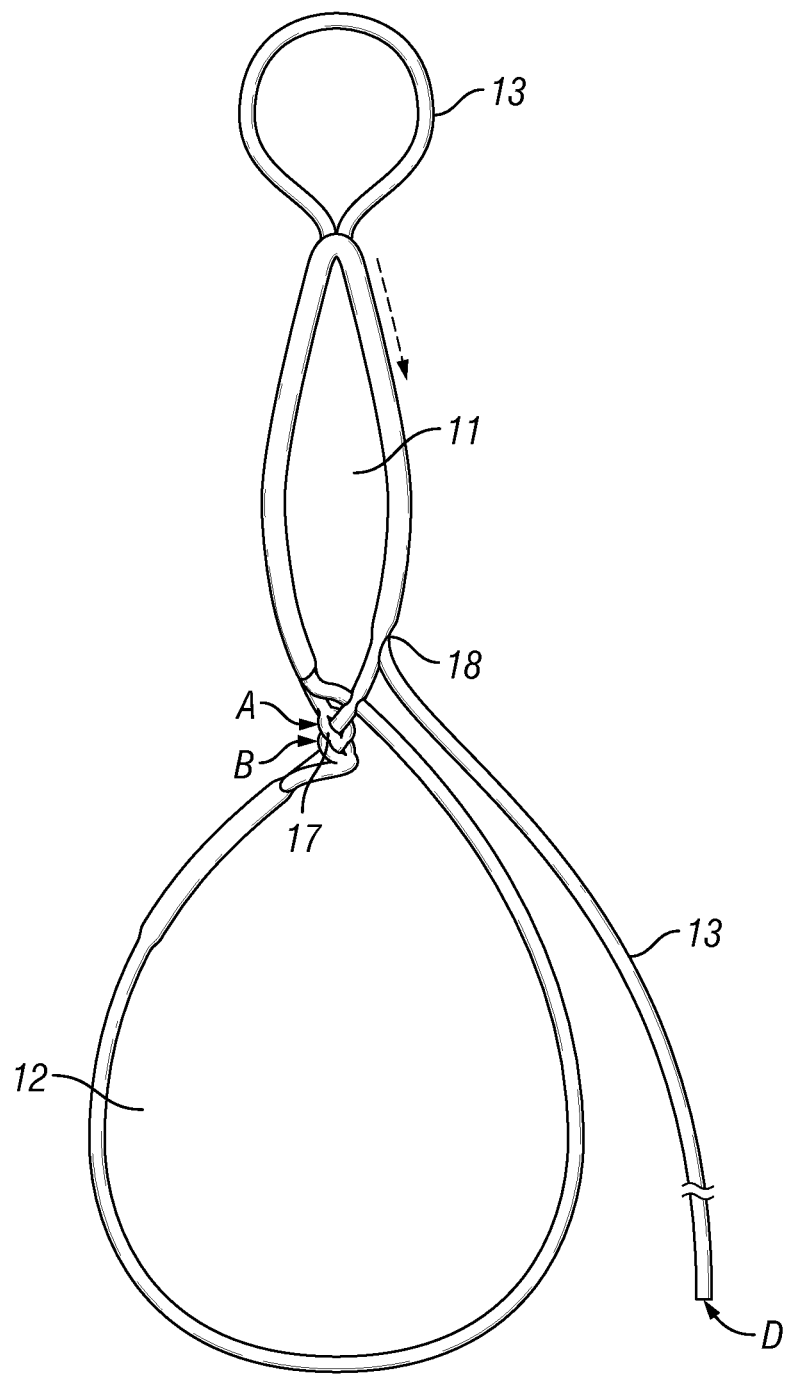
Figure 10:
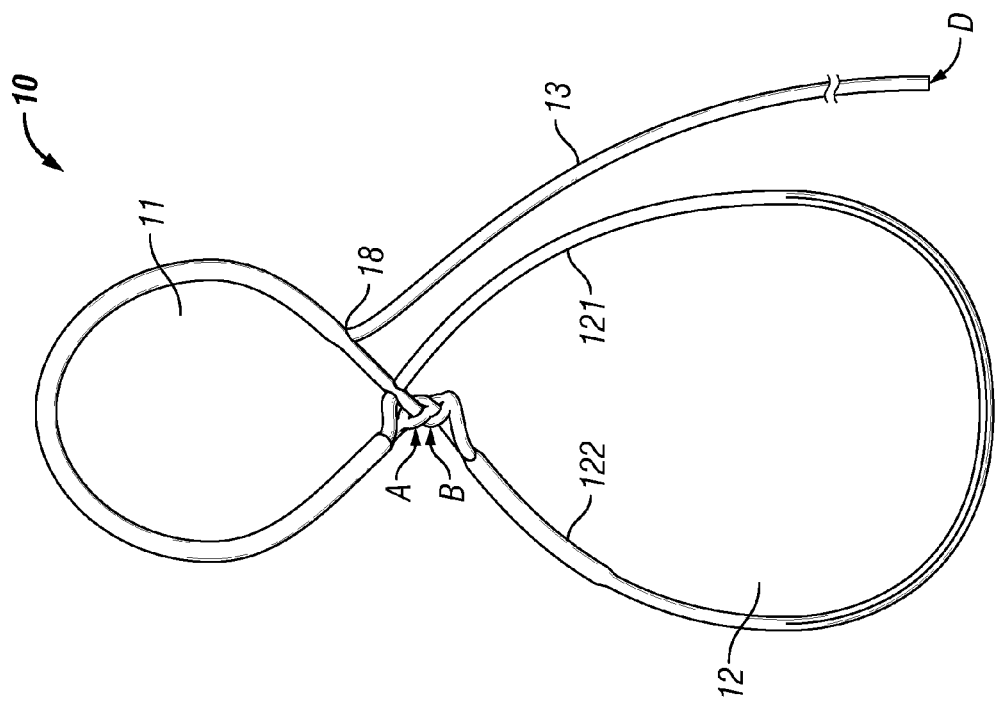

Continuing with this embodiment, FIGS. 8-10 depict the formation of the adjustable portion 12. Referring to FIGS. 4 and 7, to clarify positional locations, and FIG. 8, the single free strand 13 is passed through the filament at the first entrance point 15 of the nonadjustable portion 11 and across the crotch 17 into the filament's core at the second entrance point 19 of the nonadjustable portion 11. The second entrance point 19 is preferably a gap in the braiding created by the splice at reference point A. However, the second entrance point 19 may be disposed elsewhere along the filament above reference point A. The single free strand 13 is then run through the filament's core and extended through the braid at the end of portion 11 at the first exit location 16, opposite the crotch 17.

Referring to FIG. 9, the single free strand is then inserted back into the first exit location 16 and passed through the core of the opposite side of nonadjustable portion 11. The free strand 13 then exits the braiding approximately 2 mm from the crotch of nonadjustable portion 11 at a second exit location 18. However, this is merely one example of the second exit location of free strand 13 as the free strand 13 may exit at any location along the nonadjustable portion 11 depending on the desired angle of pull of free strand 13 and the desired anti-slippage force, which is a function of the buried length of free strand 13 within nonadjustable portion (e.g., the more length of free strand 13 buried within nonadjustable portion 11, the more friction will be present between the two filament portions, and thus, the more anti-slippage force which will be present).

The free strand 13 may then be pulled until the only loop portions that remain are the nonadjustable portion 11 and adjustable portion 12, as seen in FIG. 10. Effectively, this tensioning pulls the free strand 13 completely inside the inner core of the nonadjustable portion 11, such that the free strand no longer exits the inner core at first exit location 16. This method of assembly and braiding, from the single line of filament to completed device 10, may be such that pulling on the single free strand 13 to shrink the adjustable portion 12 goes unimpeded, but expansion of the adjustable portion 12 is restricted. For example, this expansion of the adjustable portion 12 is restricted when first side 121 and second side 122 of portion 12 are tensioned equally by a tissue graft, as would normally be the case during the various uses of the present invention, as discussed further below. However, the adjustable portion may be selectively expanded when desired by holding nonadjustable portion 11 and tensioning the first side 121 only, preferably applying such tension close to or adjacent to first entrance point 15.

Furthermore, as mentioned above, this embodiment of assembly provides a device that include a double thickness of the adjustable portion 12 (segments 13' and 14) and a "triple thickness" of the nonadjustable portion 11 (the nonadjustable portion 11 itself, along with strands 13' and 14 positioned through the inner core of nonadjustable portion 11). These multiple thicknesses may provide for added strength to device and further minimize any weaknesses which may have been present (i.e., at the splices) had the multiple thicknesses not been present. Additionally, it is important to note that positioning both strands 13' and 14 within the core of nonadjustable portion 11 also increases friction (and thus, anti-slippage force) over and above if only a single thickness strand were positioned in the core of portion 11. This is because, of course, the double thickness (strands 13', 14) may have a larger diameter, or at least will be less susceptible to radial compression, than a single thickness strand.

However, in some embodiments, this "double thickness" of free strand 13 may not extend along the entire length of the free strand 13 such that at least a portion of free strand 13 has only a single thickness. This may be present where short strand 14 does not have a length sufficient to extend to the end of strand 13'. In such embodiments, sufficient friction between the free strand 13 and the inner core of nonadjustable portion 11 may still be achieved. In one example, the portion of the filament, forming free strand 13, may be constructed of a material with a higher coefficient of friction, or is otherwise roughened to increase the friction between free strand 13 and the inner core of nonadjustable portion 11. Similarly, the nonadjustable portion 11 could also be constructed of such a material to also increase friction. In another example, the nonadjustable portion 11 could have a longer length, and thus, a longer inner core. Thus, the contact between the longer inner core and the free strand would increase, along with the overall friction between the free strand and nonadjustable portion. Other alterations to the suture device 10 in addition to the example above, to increase the friction between the free strand and the inner core of the nonadjustable member are also envisioned, and may be used where the free strand is only of a "single thickness" or where the free strand has the "double thickness."

In yet a further embodiment, the suture device 10 may include additional splices at any location along its structure, which may be useful for various purposes. For example, the end of free strand 13 (i.e., at location D in FIG. 10), may include a splice, such as an Eye splice. This Eye splice may be formed to create a loop or eyelet on the end of free strand 13 which could be used as a handle through which an instrument, finger or fingers, another suture, or the like could be positioned. Additionally, such loops or eyelets could be positioned anywhere along the length of free strand 13 to form an engagement point through which an instrument, finger or fingers, another suture, or the like could be positioned. Typically, in order for the positioning of such splices to be possible, the free strand 13 would have to be of a "single thickness" at the location of the splice.

Similarly, in other examples of this yet further embodiment, such additional splices may be positioned at other locations on the suture device other than on the free strand 13. For example, at least one eyelet may be formed at one or more positions on the adjustable portion 12 (again, the adjustable portion 12 at this position(s) would have to be of a single thickness) forming a "stop" on the adjustable portion which can limit the amount the adjustable portion can shrink upon tensioning free strand 13. Alternatively, such eyelets on the adjustable portion may serve as additional engagement points to which additional sutures, graft material, or the like may secure.

Figure 11:
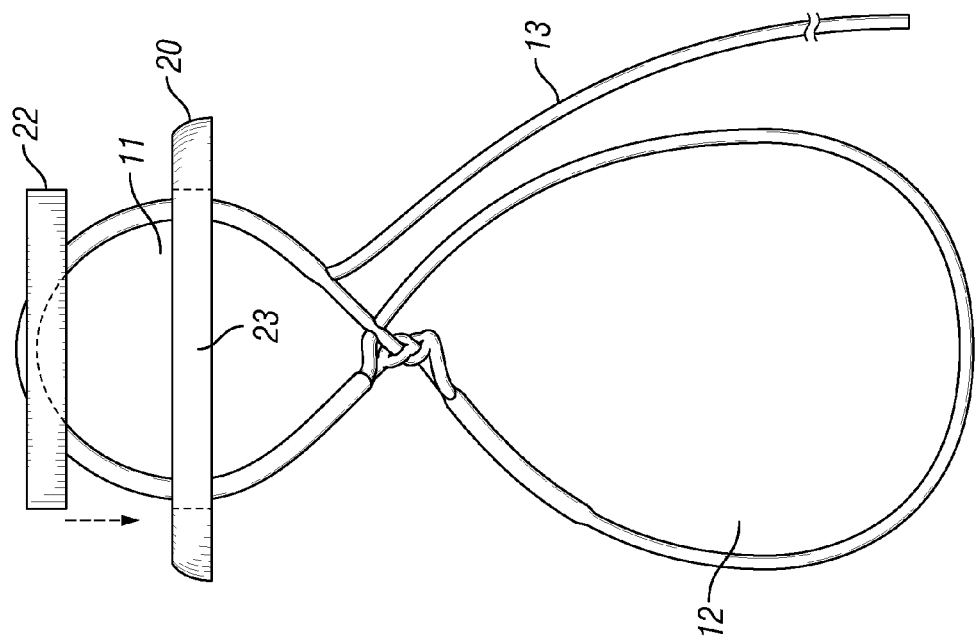
FIG. 11 shows an exemplary button anchor construct for use with the suture device of FIG. 1 in soft tissue repair.

In other embodiments, the present invention includes a system or kit including at least one suture device 10 and at least one suture anchor. One example of a suitable suture anchor for use in this embodiment is a button anchor 20, as illustrated in FIG. 11. In one example, the button anchor can be the VersiTomic G-Lok® button anchor system (Howmedica Osteonics, Mahwah, N.J.), or can be any of the various embodiments disclosed in U.S. application Ser. No. 13/182,851, filed Jul. 14, 2011, and Ser. No. 12/682,324, filed Sep. 7, 2010, the entireties of which are hereby incorporated by reference herein as if fully set forth herein, and all of which are assigned to the same entity as the present application. FIG. 11 shows an exemplary button anchor for use in soft tissue repair, such as ACL replacement surgery where the button anchor 20 may be positioned on a lateral side of the femur bone to secure an ACL graft within a bone tunnel in the femur, as is known in the art, and as is illustrated in the various incorporated references listed above.

Figure 12:
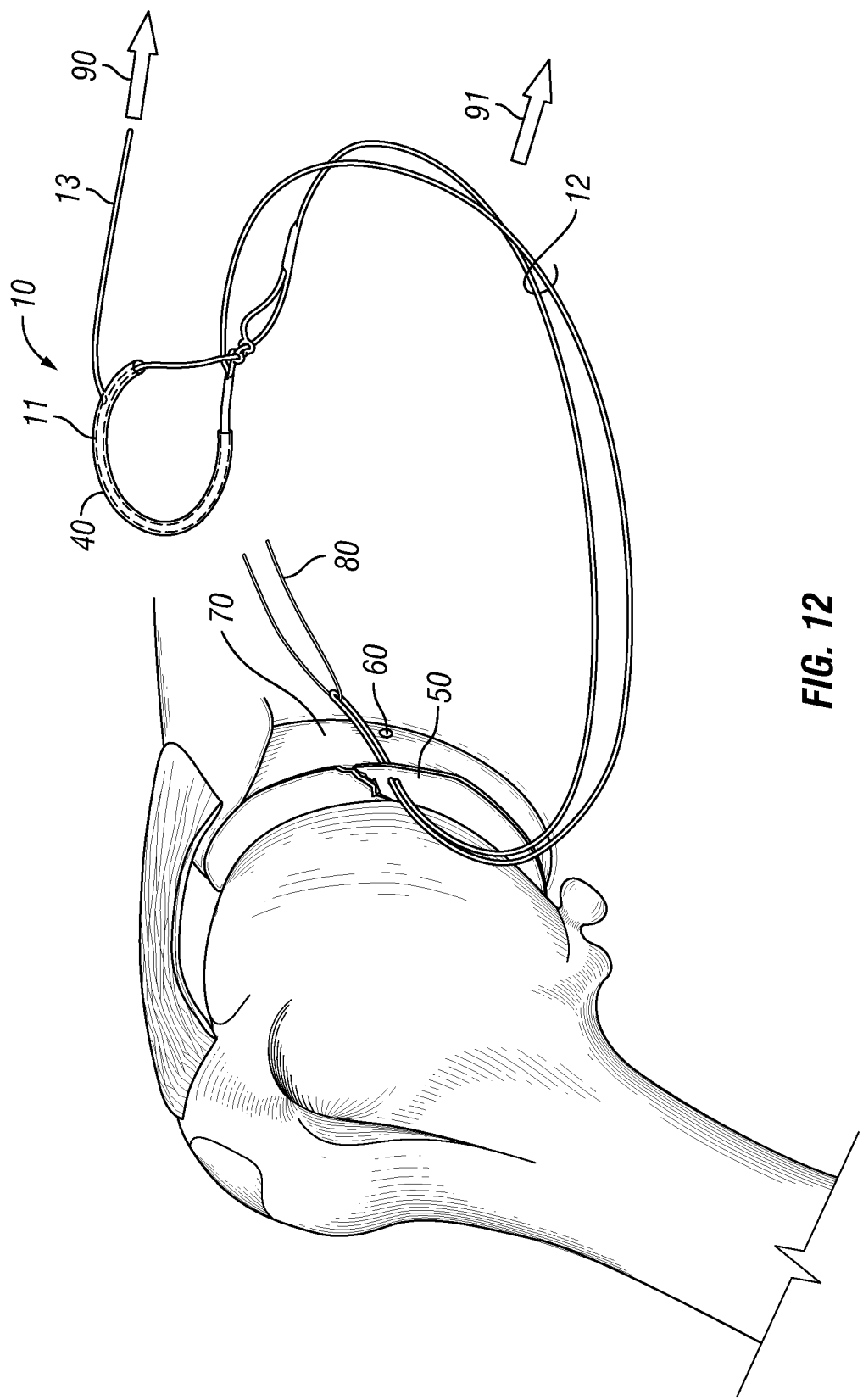
FIG. 12 illustrates one embodiment of a method of use of the suture device of FIG. 1.

Another example of a suitable suture anchor for use in a kit or system with at least one suture device 10 is filamentary fixation device, also referred to as an "all-suture" suture anchor, illustrated as filamentary sleeve 40 in FIG. 12. In one example, the filamentary sleeve 40 can be the Iconix® all suture anchor system (Howmedica Osteonics, Mahwah, N.J.). Additional examples are disclosed in U.S. Provisional Application No. 61/679,336, filed Aug. 3, 2012, U.S. application Ser. No. 13/303,849, filed Nov. 23, 2011, Ser. No. 13/588,586, filed Aug. 17, 2012, and Ser. No. 13/588,592, filed Aug. 17, 2012, and U.S. Pat. Nos. 5,989,252 and 6,511,498, the entireties of which are incorporated by reference herein as if fully set forth herein and all of which are assigned to the same entity as the present application. FIG. 12 shows an exemplary filamentary sleeve 40, positioned on nonadjustable portion 11, for use in soft tissue repair, where the all suture anchor 40 may be deployed, for example, within a bone void to secure soft tissue to bone, as is known in the art.

Such a system and/or kit can also include a plurality of suture devices 10 and/or a plurality of suture anchors, such as buttons 20, sleeves 40, and the like. Each suture anchor may be packaged, and arrive to the operator, fixedly secured to at least one suture device 10 (i.e., as an assembly), though the suture anchor and suture device may also be packaged separately for assembly by the operator.

Such systems or kits, particularly when a suture anchor like button anchor 20 or filamentary sleeve 40 is used, the nonadjustable portion 11 may have to be secured to the button 20 or sleeve 40 in some manner, and likely, such securement would occur during manufacture and assembly and prior to delivery to the operator. In one embodiment, with reference to FIG. 11, the present invention includes a method of assembly, where the method includes the nonadjustable portion 11 being positioned through a throughbore 23 in the anchor 20 and an insert 22 (having an internal saddle, designated by the dotted line, over which the nonadjustable portion 11 can be positioned) would be positioned within the portion 11. The insert 22 and anchor 20 would then be connected (i.e., the insert 22 would be positioned and secured within throughbore 23 via a snap-fit or the like) to secure the nonadjustable portion 11 to the anchor 20. This assembly can be performed during manufacture, or alternatively, by the operator, and is similar to the method of assembly illustrated and described in the above-cited '851 application, incorporated by reference herein. Alternatively, rather than positioning nonadjustable portion 11 in throughbore 23, the nonadjustable portion 11 may be connected to slots disposed within opposite ends of anchor 20 (not shown). Further, nonadjustable portion 11 may be secured to anchor 20 utilizing any of the other methods previously described (e.g., by passing strand 13' through a portion of anchor 20 prior to passing strand 13' into and through the inner core of nonadjustable portion 11).

In another alternative embodiment, the method of assembly can include performing the above steps, as illustrated in FIGS. 2-10, in the presence of a button anchor such that, during the formation of the nonadjustable portion (FIG. 3), the single line of filament passes through at least a portion of an anchor to secure the nonadjustable portion 11 thereto. In this embodiment, a button anchor including an insert (as in FIG. 11) may not be required since the filament can merely be threaded through one or more slots, eyelets, portions, or the like of anchor 20 (as known in the art) during the step illustrated in FIG. 3. Such a method of assembly may be useful when combining the device 10 with an anchor 20 such as is disclosed and illustrated in the above-cited '324 application, incorporated by reference herein.

Referring to FIG. 12, an embodiment of a method of assembly utilizing filamentary sleeve 40 would employ a similar construction to that of the above alternative embodiment. Specifically, the method of assembly can include performing the above steps, as illustrated in FIG. 2-10, in the presence of sleeve 40 such that, during the formation of the nonadjustable portion 11 (FIG. 3), the single line of filament passes through at least a portion of sleeve 40 to secure the nonadjustable portion 11 thereto. Further, during the steps associated with passing the free strand 13 through nonadjustable portion 11 (as in FIGS. 8-10), the free strand 13 would exit from both the nonadjustable portion and sleeve 40 at first exit location 16, and would likewise exit both the nonadjustable portion and sleeve at the second exit location 18, which results in the arrangement illustrated in FIG. 12. Alternatively, since the second exit location 18 may be positioned anywhere along nonadjustable portion 11, the second exit position 18 may be positioned outside the length of sleeve 40, such that the free strand exits from the nonadjustable portion outside the length of the sleeve. However, FIG. 12 illustrates a preferred arrangement (i.e., where second exit location 18 is positioned such that the free strand 13 exits through sleeve 40) because positioning the free strand as such allows the nonadjustable portion to be tensioned, to deploy sleeve 40 in bone, while keeping the free strand 13 tightly within the now-compressed sleeve 40 (following deployment). Examples of such deployment may be found in the above-cited applications incorporated by reference herein.

In another embodiment, the present invention is a method of use to repair soft tissue. In this embodiment, suture device 10, as exemplified in FIG. 1, may be utilized in soft tissue repair surgery, such as ACL replacement surgery, rotator cuff repair surgery, labrum (hip or shoulder) repair surgery, and the like. While it is envisioned that the devices (such as device 10), systems and kits (e.g., including a suture anchor) of the present invention can be used to repair any soft tissue in which a suture construct can be used, the exemplary method of use in the attachment of an ACL graft will be described, and specifically the attachment of the ACL graft in a bone tunnel formed in a femur bone. It should be understood that this method may also be used to secure the ACL graft in a similar bone tunnel formed in the tibia bone.

During such procedure, it is preferred to use the system or kit illustrated in FIG. 11, such that a button anchor 20 and suture device 10 are used. Initially, the ACL graft is positioned through adjustable portion 12 and the button anchor 20 is passed through a tunnel in the femur (either via a medial-lateral entry point or through a bone tunnel formed in the tibia) and secured to the lateral cortex of the femur bone, as is known in the art. The adjustable portion 12 and single free strand 13 extend through the femoral tunnel along with the ACL graft. In an alternative, the adjustable portion 12 may have a sufficient length such that the portion 12 and free strand 13 extend out of the femoral tunnel and to the operator, such that the graft can be loaded onto portion 12 following placement of button anchor 20 on the lateral cortex of the femur. In this alternative, the single free strand 13 would then be pulled, which contracts the adjustable portion 12 moving the tissue graft through the tunnel(s) until the graft is generally positioned within the femoral and tibial tunnel.

In any event, once the graft is generally positioned in the tunnels, the adjustable portion 12 may be tensioned to adjust the positioning of the graft further to what should result in generally the proper, final positioning, which is generally defined by a hard-stop, for example the end of a bone tunnel, the end of a step in the bone tunnel (as known in the art) or contact of the graft with crotch 17 of device 10. However, it should be noted that where an operator does not strictly rely on the hard-stop for final positioning, he or she should maintain an amount of additional length to the adjustable portion 12 as the device 10 provides for simplified tensioning of free strand 13 (i.e., shrinking the adjustable loop 12), but loosening of the strand (i.e., expanding the adjustable loop 12) is more difficult. Following general positioning of the graft, the opposite end of the graft, in the tibial tunnel, is secured thereto. In the tibial tunnel, a traditional interference screw, or like method, may be used as is known in the art. Alternatively, another button anchor, and optionally, another suture device 10, may be used for additional flexibility in adjusting the tension of the graft, as will be discussed below.

Once the tibial end of the graft is secured, and in the event an amount of adjustable portion 12 remains due to not arriving at the hard-stop (e.g., end of bone tunnel, step in bone tunnel, crotch 17, etc.), the free strand 13 can be further tensioned as desired by the operator to achieve the appropriate tension of the graft. If a second assembly of button anchor and device was used in the tibial tunnel, the free strand of that assembly may also be tensioned as desired. As discussed above, the device 10 includes a one-way feature (i.e., the constricting nature of the braid itself) such that the adjustable portion 12 can shrink by simply tensioning free strand 13, but the assembly of device 10 prevents the adjustable portion 12 from expanding, particularly from tension applied to the adjustable portion 12 (i.e., through tension applied by the graft). As such, if the operator over-tensioned the free strand 13, and thus needs to expand adjustable loop 12 by a certain amount, the operator must access the first side 121 and only apply tension on the first side 121 of the adjustable loop 12 to "release" the one-way locking feature and ease tension on the adjustable portion 12. Any surgical instrument suitable to travel into the bone tunnel or joint space, such as a grasper, or the like, can be used.

Generally, once appropriate tension is acquired, the adjustable portion 12 does not need to be tied off to prevent expansion of the adjustable portion 12 due to the constricting nature of the braid. Thus, the excess length of the free strand 13 can simply be cut and removed. Alternatively, for added security if desired by the operator, a half-hitch, or similar knot, can be tied around the adjustable portion using the free strand 13 and then the excess length of the free end 13 can be cut and removed.

Another embodiment of a method of use is illustrated in FIG. 12. In this embodiment, suture device 10, as exemplified in FIG. 1, may be utilized to reattach soft tissue to bone. In practicing this method, it is preferred to use the system or kit illustrated in FIG. 12, such that a filamentary sleeve 40 and suture device 10 are used. Initially, a lead suture 80 is positioned through the adjustable portion 12. The adjustable portion 12 is then passed around or through the tissue 50 by pulling on the lead suture 80 using a needle (not shown) or the like attached to lead suture 80. While the lead suture 80 (with needle) is depicted as the suture passing device, it is to be understood that other instruments may be used to pass the adjustable portion 12 through tissue 50, such as a suture shuttle, suture passer instrument, or the like. A hole 60 is drilled into bone 70 at a location desirable for anchoring tissue 50 to bone 70, which may be performed before or after the adjustable portion 12 is passed through tissue 50. With the adjustable portion 12 disposed at an opposite side of the tissue 50 from the nonadjustable portion 11 and sleeve 40, the nonadjustable portion 11 and sleeve are passed through the adjustable portion 12, thereby wrapping a portion of the adjustable portion 12 around a portion of the tissue 50 forming a knotless lock, similar to a "luggage tag" configuration. The sleeve 40 may then be inserted into the hole 60 such that a portion of nonadjustable portion 11, the single free strand 13 and adjustable portion 12 extend from hole 60. The sleeve 40 is then deployed by tensioning a portion of the adjustable portion 12 that is not wrapped around the tissue 50, as demonstrated by arrow 91. Once the sleeve 40 is firmly anchored within hole 60, the free strand 13 is tensioned, as demonstrated by arrow 90, thereby drawing the tissue 50 into therapeutic engagement with bone 70 by shrinking the adjustable portion 12. Generally, the excess length of the free strand 13 may be cut and removed without the need to be tied off due to the constricting nature of the braid, though additional securement through a knot using free strand 13 may be performed if desired.

In an alternative embodiment, once the sleeve 40 is positioned within bone hole 60, rather than tensioning the filaments of adjustable portion 12, as illustrated by arrow 91, this step can be bypassed. Instead, once sleeve 40 is in hole 60, free strand 13 may be tensioned, as illustrated by arrow 90, which shrinks the adjustable portion 12 and draws the tissue 50 towards the bone 70. As the loop 12 shrinks, and the tissue 50 is tensioned against the bone, the nonadjustable portion 11 may also be drawn in an upward direction (i.e., out of the hole 60), by the various forces associated with the adjustable portion 12. This upward movement of the nonadjustable portion 11 may deploy the sleeve 40, and thus, a single motion of tensioning free strand 13 both deploys sleeve 40 and draws the tissue 50 to the bone 70 to complete the repair.

In another alternative embodiment to the method illustrated in FIG. 12, such a method may be performed using an alternative configuration of the suture device 10 and sleeve 40. Specifically, in this alternative, the sleeve 40 can instead be positioned along a portion of the adjustable portion 12, rather than on the nonadjustable portion 11. This configuration may be assembled, for example, during manufacture of device 10 such that, prior to the step of passing single free strand 13 through the filament at the first entrance point 15 of the nonadjustable portion and across the crotch 17 into the filament's core at the second entrance point 19 of the nonadjustable portion 11, as illustrated in FIGS. 7 and 8, sleeve 40 can be positioned along a portion of single free strand 13. Thus, once the free strand 13 is positioned into the core of nonadjustable portion 11, the sleeve 40 will be positioned on adjustable portion 12.

Continuing with this alternative embodiment using this alternative configuration of suture device 10 and sleeve 40, at least the nonadjustable portion 11 may be passed through or around the tissue. Similar to above as to FIG. 12, with the nonadjustable portion 11 disposed at an opposite side of the tissue 50 from the adjustable portion 12 and sleeve 40, the adjustable portion 12, free strand 13, and sleeve are passed through the nonadjustable portion 11, thereby wrapping a portion of the nonadjustable portion 11 around a portion of the tissue 50 forming a knotless lock, similar to a "luggage tag" configuration. It should be noted that, depending on the actual positioning of the free strand 13 exiting from the nonadjustable portion (i.e., the second exit location 18), the free strand 13 may not pass through the nonadjustable portion along with the adjustable portion 12, but instead may be positioned at a location adjacent the tissue 50 along some aspect of the "luggage tag" configuration. The sleeve 40 may then be inserted into the hole 60 such that a portion of adjustable portion 12 extends from hole 60. The sleeve 40 is then deployed by tensioning the portion of the adjustable portion 12 exiting from hole 60. Once the sleeve 40 is firmly anchored within hole 60, the free strand 13 is tensioned, thereby drawing the tissue 50 into therapeutic engagement with bone 70 by shrinking the adjustable portion 12. During this tensioning step, the adjustable portion 12 can slide freely through the deployed sleeve 40. Generally, the excess length of the free strand 13 may be cut and removed without the need to be tied off due to the constricting nature of the braid, though additional securement through a knot using free strand 13 may be performed if desired.

In yet another embodiment of a method of the present invention, following either of the above-described repairs utilizing sleeve 40, rather than cutting the excess length of free strand 13, the excess length can be passed through another portion of the anatomy, such as through a second location on the portion of soft tissue 50. This may be utilized where the damage to the soft tissue is extensive and requires more than just a single point of securement. For example, once the excess length is passed through the tissue, a common surgical knot can be used to draw the tissue 50 at the second location towards bore hole 60. In another example, once the excess length is passed through the tissue, the excess length of the free strand 13 may then be passed through a second suture sleeve, and such second sleeve can be positioned and deployed in a second bore hole in bone 60. Then, the excess length of free strand 13 may be tensioned through the second sleeve and secured to now provide two points of reattachment of tissue 50. Generally, these steps of passing the free strand 13 through a sleeve, deploying the sleeve and tensioning the free strand through the sleeve may be performed, for example, as disclosed in the various above applications incorporated by reference, such as the '336 Provisional Application and the '586 and '592 Applications. Another example of these steps is generally disclosed in U.S. patent application Ser. No. 13/783,804, filed on Mar. 4, 2013, the entirety of which is hereby incorporated by reference herein as if fully set forth herein, and which is assigned to the same entity as the present application. This step may be repeated as necessary and so long as there is excess length of free strand 13 available, though of course a second length of filament may be used in cases of, for example, exceptionally large tears in the soft tissue 50.

In yet a further embodiment of a method of the present invention, similar to any of the above-described repairs utilizing sleeve 40, sleeve 40 may instead be engaged with device 10 prior to the completion of the construct of device 10. Specifically, in this embodiment, sleeve 40 is positioned on the nonadjustable portion 11, as in FIG. 12, but the free strand 13 is not yet positioned through nonadjustable portion 11. Thus, in this arrangement, the device 10 may resemble that of FIG. 7 (though sleeve 40 is positioned on nonadjustable portion 11 (not shown)).

This embodiment differs from that of FIG. 12, however, because the device 10 is not positioned on the tissue 50 in the aforementioned "luggage tag" configuration. Rather, free strand 13 (as in FIG. 7) is passed around or through tissue 50 as a length of filament would be as normally performed in the art. Also in this embodiment, a suture shuttle (not shown) would be positioned through the inner core of nonadjustable portion 11, and thus, also through sleeve 40. The positioning of such a suture shuttle would be similar to the positioning of free strand 13 as illustrated in FIG. 10, for example. The suture shuttle may be any type of suture shuttle in the art, such as those described in the above applications incorporated by reference, such as the '336 Provisional Application and the '804, '586 and '592 Applications, though other structures such as a simple metal wire having a looped end may be used.

In this configuration, the end of free strand 13, already positioned around or through tissue 50, may then be engaged with the suture shuttle. The shuttle may then be tensioned to pull the free strand 13 through the inner core of nonadjustable portion 11 to the configuration of FIG. 10. It should be noted that this shuttling step can occur prior to or after sleeve 40 positioned and deployed in the bore hole 60 in bone 70. The free strand 13 may then be tensioned to shrink the adjustable portion 12, and in this configuration, the adjustable portion 12 may freely slide through both tissue 50 and sleeve 40 (and the inner core of nonadjustable portion 11) to secure the tissue to bone 70. As above, the free strand 13 may then either be cut, and disposed of, or may be passed through the tissue 50 again for a second anchor, such as a second sleeve 40 or the like.

It should be noted that the above methods, such as is disclosed in FIG. 12, may be performed as an arthroscopic procedure, and further, while the repair may be used on any tissue for reattachment to another tissue, FIG. 12 illustrates the method as used in the shoulder or hip for the repair and reattachment of labrum tissue to the glenoid or acetabulum.

Suture device 10 is advantageous for such methods of surgery because the single free strand 13 is the only strand uses for adjusting the adjustable portion 12. Further, the adjustable portion 12 is continuous and made from one strand as well, which lessens the possibility of entanglement, e.g., within the narrow bone tunnels for ACL surgery (as in FIG. 11) and/or during arthroscopic surgical procedures (as in FIG. 12). Additionally, because suture device 10 is constructed by splicing a single length of filament, the construction is strong and durable and requires no additional components reducing the likelihood of failure.

In another embodiment, the present invention includes a system for the repair of soft tissue including at least one adjustable continuous filament assembly, at least one instrument for insertion of the adjustable continuous filament assembly, and a surgical procedure. The system may also include at least one suture anchor. The surgical procedure may include instructions or protocol for using the adjustable continuous filament assembly and instrument (and optional suture anchor) to repair soft tissue. The protocol may include aspects of any of the above-discussed embodiments, though other variations are also envisioned within the scope of the present invention.

In an associated embodiment, the present invention includes a method of providing instructions or information to practice any of the various methods of assembly or performing soft tissue repair described herein. For example, the method may include supplying a surgical protocol, or like document, to provide step-by-step instructions for performing any of the method embodiments of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A continuous filament assembly, comprising:
a single line of filament having an nonadjustable loop, an adjustable loop, and a single free segment, the adjustable loop having a first portion and a second portion, the first portion extending from the nonadjustable loop to a first position along an outer wall of the nonadjustable loop, and the second portion entering into the outer wall of the nonadjustable loop and extending through at least a portion of an inner core of the nonadjustable loop to a second position along the outer wall of the nonadjustable loop, the single free segment extending from the outer wall of the nonadjustable loop at the second position such that the free segment is continuous with the second portion of the adjustable loop, wherein pulling the free segment shrinks the first portion of the adjustable loop.

2. The continuous filament assembly of claim 1, wherein the nonadjustable loop is formed by a locking splice.

3. The continuous filament assembly of claim 2, wherein the nonadjustable loop is formed by a locking Brummel splice, a stitched buried splice, or a lock stitch tuck splice.

4. The continuous filament assembly of claim 1, wherein the second portion of the adjustable loop is positioned through the inner core of the nonadjustable loop to form a one-way feature such that the free segment is tensionable to shrink the adjustable loop, but the one-way feature prevents the adjustable loop from expanding due to tension applied to the adjustable loop.

5. The continuous filament assembly of claim 1, wherein the first position and second position are spaced from one another along the nonadjustable loop.

6. The continuous filament assembly of claim 1, further comprising a suture anchor disposed along a portion of the outer wall of the nonadjustable loop.

7. The continuous filament assembly of claim 6, wherein the anchor is a button anchor.

8. The continuous filament assembly of claim 6, wherein the anchor is a filamentary sleeve.

9. A continuous filament assembly, comprising:
a single line of filament having a first segment defining a first loop, a second segment defining a second loop, and a free segment, the second segment extending from the first loop to a first position along an outer wall of the first segment, the second segment coupled to the free segment at the first position and passing through the sidewall of the first segment into a core thereof and extending along the core to a second position at which the free segment extends out of the core and through the sidewall of the first segment.

10. The assembly of claim 9, wherein the second segment is joined to the first loop by a lock.

11. The assembly of claim 10, wherein the lock is a locking Brummel splice.

12. The assembly of claim 10, further comprising a third segment extending from the lock and being buried into a core of the second segment.

13. The assembly of claim 9, further comprising a suture anchor disposed along a portion of the outer wall of the first segment.

14. The assembly of claim 13, wherein the suture anchor is one of a button anchor and filamentary sleeve.

15. A continuous filament assembly, comprising:
a first segment of filament defining a first loop and having a sidewall defining a core extending along a length thereof;
a second segment of filament extending from the first loop and defining a second loop; and
a free segment of filament extending through the core of the first segment and being coupled to the second segment such that tensioning the free segment shrinks the second loop defined by the second segment.

16. The assembly of claim 15, wherein the first loop is further defined by a lock disposed between the first loop and second loop, the lock being configured to constrain the first loop from expansion or contraction.

17. The assembly of claim 16, wherein the lock is a locking Brummel splice.

18. The assembly of claim 16, wherein the free segment passes through the sidewall into the core of the first segment at an entrance location disposed adjacent to the lock and extends through the core to an exit location at which the free segment passes through the sidewall and out of the core.

19. The assembly of claim 18, wherein the lock defines a crotch of the first loop and the free segment passes through the sidewall of the first segment and extends across the crotch to the entrance location.

20. The assembly of claim 15, wherein the first, second and free segments of filament comprise a single line of filament.

\* \* \* \* \*